US012758201B2

(12) United States Patent
Wamser

(10) Patent No.: US 12,758,201 B2
(45) Date of Patent: Oct. 13, 2026

(54) CONSOLE AND FOOT-OPERATED CONTROL UNIT FOR A MEDICAL TREATMENT SYSTEM AND MEDICAL TREATMENT SYSTEM THEREFOR

(71) Applicant: Carl Zeiss Meditec AG, Jena (DE)

(72) Inventor: Michael Wamser, Aalen (DE)

(73) Assignee: Carl Zeiss Meditec AG, Jena (DE)

( * ) Notice: Subject to any disclaimer, the term of this patent is extended or adjusted under 35 U.S.C. 154(b) by 837 days.

(21) Appl. No.: 17/950,063

(22) Filed: Sep. 21, 2022

(65) Prior Publication Data

US 2023/0089567 A1 Mar. 23, 2023

(30) Foreign Application Priority Data

Sep. 21, 2021 (DE) ..................... 10 2021 124 421.8

(51) Int. Cl.
*A61B 17/00* (2006.01)
*A61F 9/00* (2006.01)

(52) U.S. Cl.
CPC .... *A61B 17/00* (2013.01); *A61B 2017/00199* (2013.01); *A61B 2017/00221* (2013.01); *A61B 2017/00973* (2013.01); *A61F 9/00* (2013.01)

(58) Field of Classification Search
CPC .......... A61B 17/00; A61B 2017/00199; A61B 2017/00221; A61B 2017/00973;
(Continued)

(56) References Cited

U.S. PATENT DOCUMENTS 6,018,227 A * 1/2000 Kumar .............. H01M 10/4257
320/112
8,565,839 B2 10/2013 Ma et al.
(Continued)

FOREIGN PATENT DOCUMENTS

WO 2013134133 A1 9/2013
WO 2014172550 A1 10/2014

OTHER PUBLICATIONS

Office Action issued in German Patent Application No. DE 10 2021 124 421.8, dated May 4, 2022 (from which this application claims priority) and English language translation thereof.
(Continued)

*Primary Examiner* — Adam Z Minchella
*Assistant Examiner* — Ashleigh Lauren Kern
(74) *Attorney, Agent, or Firm* — Ewers IP Law PLLC; Falk Ewers

(57) ABSTRACT

A console for a medical treatment system includes a console housing and a control unit for controlling a medical treatment instrument. A foot-operated control unit wirelessly coupled to the control unit, and the console housing has at least one side wall, which has a bearing surface for arranging the foot-operated control unit in a not-in-use position. The bearing surface is inclined with respect to a horizontal plane, at least in the region where the foot-operated control unit is arranged, in order when arranging the foot-operated control unit on the bearing surface to bring about bearing of the foot-operated control unit against the bearing surface by the weight of the foot-operated control unit. The side wall has in the region of the bearing surface a console-side connecting unit for releasably connecting the foot-operated control unit to the console. Further, a corresponding foot-operated control unit and a medical treatment system are provided.

8 Claims, 7 Drawing Sheets

(58) Field of Classification Search
CPC .......... A61B 90/50; A61B 2017/00477; A61B 2017/00977; A61B 3/102; A61B 5/0053; A61B 5/03; A61B 5/7455; A61B 2017/00017; A61B 2017/00119; A61B 2017/00123; A61B 2017/00398; A61B 2505/05; A61B 2562/0247; A61F 9/00; A61F 9/00736; A61F 9/00745; A61F 9/008; A61M 2210/0612; G05G 1/305; G05G 1/30; G06F 3/0334
See application file for complete search history.

(56) References Cited

U.S. PATENT DOCUMENTS

| | | | | |
|---|---|---|---|---|
| 2004/0212344 | A1 | 10/2004 | Tamura et al. | |
| 2006/0219049 | A1 | 10/2006 | Horvath et al. | |
| 2008/0114387 | A1* | 5/2008 | Hertweck | A61F 9/00745 606/1 |
| 2011/0087069 | A1* | 4/2011 | Hamel | A61B 90/70 600/118 |
| 2011/0134601 | A1* | 6/2011 | Sa | G06F 1/1632 361/679.43 |
| 2017/0207467 | A1* | 7/2017 | Shelton, IV | A61B 17/320092 |
| 2018/0042802 | A1 | 2/2018 | St. Louis et al. | |
| 2019/0350757 | A1 | 11/2019 | Charles | |

OTHER PUBLICATIONS

European Search Report dated Feb. 10, 2023 of European counterpart application No. EP 22196208.7, and English language translation thereof.

* cited by examiner

CONSOLE AND FOOT-OPERATED CONTROL UNIT FOR A MEDICAL TREATMENT SYSTEM AND MEDICAL TREATMENT SYSTEM THEREFOR

CROSS REFERENCE TO RELATED APPLICATIONS

This application claims priority to German patent application 10 2021 124 421.8, filed Sep. 21, 2021, the entire content of which is incorporated herein by reference.

TECHNICAL FIELD

The disclosure relates to a console for a medical treatment system, in particular an ophthalmosurgical system for the treatment of an eye, with a console housing and a control unit for controlling a medical treatment instrument, wherein a foot-operated control unit can be wirelessly coupled to the control unit, and the console housing has at least one side wall. The disclosure also relates to a foot-operated control unit for a medical treatment system, in particular an ophthalmosurgical system for the treatment of an eye, with a housing, an electrical energy store arranged in the housing, an actuating element which can be actuated with a foot, a communication unit for wireless communication with a console of the medical treatment system and also a charging unit for charging the electrical energy store. Finally, the disclosure also relates to a medical treatment system, in particular an ophthalmosurgical system, for the treatment of an eye, with at least one medical treatment instrument, a console for connecting and operating the medical treatment instrument during an as-intended operating mode, a foot-operated control unit for at least partially controlling the as-intended operating mode of the medical treatment instrument, wherein the foot-operated control unit can be wirelessly coupled to the console and has an electrical energy store for supplying the foot-operated control unit with electrical energy, at least during the as-intended operating mode of the medical treatment system.

BACKGROUND

Medical treatment systems, ophthalmosurgical systems for the treatment of an eye, consoles and also foot-operated control units therefor are extensively known in the related art, and so there is no need for separate documentary evidence in this respect. Medical treatment systems serve the purpose of allowing a wide variety of treatments, for example operations, to be carried out on a body of a living being, for example a human or an animal. Often used for this is a medical treatment instrument which, during an operation, can be guided manually or with a robot. For the as-intended operating mode of the medical treatment instrument, it is often required to supply the medical treatment instrument with electrical energy, one or more treatment fluids and also operating data. Generally serving for this purpose is the console, to which the medical treatment instrument can be coupled, at least during the as-intended operating mode. The console is consequently designed for connecting and operating the medical treatment instrument.

For this purpose, the console generally has a control unit for controlling the medical treatment instrument. The control unit is in communication connection with the medical treatment element, in order for example to transmit control data to the treatment instrument, or else to obtain and evaluate operating data or measurement data from the medical treatment instrument. The console additionally makes it possible to act on the control unit in order to be able to implement the desired as-intended operating mode of the medical treatment instrument.

For this purpose, the console may have an input unit, which makes it possible for example for an operator to be able to perform settings with respect to the desired as-intended operating mode. The input unit may for example be designed to enable the operator to perform a manual input. In the case of certain medical treatments, however, manual inputs are only poorly possible or even sometimes impossible. For this reason, an input unit may be provided in the form of a foot-operated control unit which, dependent on actuation with a foot, provides a control signal for the control unit of the console. The foot-operated control unit may in this case be a component part of the console or else be formed as a separate unit. For the as-intended operating mode, the foot-operated control unit may be coupled to the console in a predeterminable way. Often provided for this is/are one or more lines, which serve for example for supplying the foot-operated control unit with electrical energy and/or for transmitting data or signals. Such lines often prove to be disadvantageous during the use of the medical treatment system. For this reason, US 2006/0219049 A1 for example discloses a footswitch for controlling a surgical system. The footswitch detects a mechanical input performed with a foot and delivers a control signal for the medical instrument by way of a wireless communication device.

In addition, it is known that the foot-operated control unit has an electrical energy store of its own, which provides electrical energy for the as-intended operating mode. The electrical energy store is generally formed by a chargeable storage battery. In this connection, US 2004/0212344 A1 for example describes an apparatus and method for maintaining a defibrillator battery charge and optionally communicating. Furthermore, U.S. Pat. No. 8,565,839 B2 describes power management for wireless devices.

Ophthalmosurgical systems and also methods for their operation are likewise known in the related art, and so there is also no need for separate documentary evidence in this respect. Various surgical techniques are known for treatment of a clouding of the crystalline lens, also known in medicine as a cataract. The most widespread technique is phacoemulsification, in which a thin hollow needle is introduced into a capsular bag, in which the crystalline lens is arranged, and is induced to undergo ultrasonic vibrations. The lens can be emulsified with the vibrating hollow needle, and lens particles released in the process can be aspirated through an aspiration line with a pump. In the process, an irrigation fluid is supplied. The lens particles are aspirated, together with the fluid, as aspiration fluid. As soon as the lens has been completely emulsified and removed, a new artificial lens can be inserted into the then emptied capsular bag. The treated patient can in this way recover good vision. While carrying out such an operation with the ophthalmosurgical system, a handpiece which has the hollow needle and, at least during the as-intended operating mode, is connected to a corresponding console of the ophthalmosurgical system is used as medical treatment instrument. The console in this case provides the irrigation fluid and likewise a discharge of the aspiration fluid. In addition, the console also provides electrical energy for the as-intended operating mode of the handpiece. With a control unit of the console, the operation of the handpiece can be controlled. Since the surgeon's hand is generally not available for controlling inputs for the operation to be carried out, a foot-operated control unit is often used to control the operation of the handpiece. For this purpose, the foot-operated control unit is correspondingly coupled to the console.

Even if the related art shows a foot-operated control unit which can be wirelessly coupled to the console, disadvantages nevertheless remain. This applies both to the storing of the foot-operated control unit in a not-in-use position and to the supplying of electrical energy to the electrical energy store, in order that the foot-operated control unit is available again for subsequent use. In this connection, U.S. Pat. No. 8,565,839 B2 for example describes an inductive coupling of the foot-operated control unit to a corresponding charging device. The use of an inductive charging device proves to be disadvantageous to the extent that structural measures have to be taken to allow corresponding coils to be incorporated in the foot-operated control unit and in the charging device. The charging device additionally requires a complex energy converter. Finally, it should be borne in mind that the inductively supplied energy also entails limited efficiency and, in addition, can cause disturbances, in particular with respect to electromagnetic compatibility. The use of such a charging device is therefore generally not unproblematic during the as-intended operating mode.

Line-bound charging of the foot-operated control unit also proves to be disadvantageous, however, since a corresponding line-bound energy supply must be ensured. This however again requires the use of electrical lines in the form of cables that has already been recognized as unfavorable. Finally, such lines may also be unfavorable with regard to electromagnetic compatibility.

Furthermore, reference is made to the documents US 2011/0087069 A1 and WO 2013/134133 A1.

SUMMARY

The disclosure addresses the problem of improving the arrangement of the foot-operated control unit, in particular when it is not in the as-intended operating mode, in particular also for supplying energy.

As a solution, the disclosure provides a console, a foot-operated control unit and also a medical treatment system as described herein.

With respect to a console of the type in question, with the disclosure it is provided in particular that the side wall has a bearing surface for arranging the foot-operated control unit in a not-in-use position, wherein the bearing surface is inclined with respect to a horizontal plane, at least in the region where the foot-operated control unit is arranged, in order when arranging the foot-operated control unit on the bearing surface to bring about bearing of the foot-operated control unit against the bearing surface by the weight of the foot-operated control unit, wherein the side wall has in the region of the bearing surface a console-side connecting unit for releasably connecting the foot-operated control unit to the console.

With respect to a foot-operated control unit of the type in question, with the disclosure it is provided in particular that the housing has a connecting region for releasably arranging the foot-operated control unit in a not-in-use position on a bearing surface of the console, wherein the connecting region has a connecting unit on the foot-operated control unit side for releasably connecting the foot-operated control unit to the console.

With respect to a medical treatment system of the type in question, with the disclosure it is provided in particular that at least the console or the foot-operated control unit is designed according to the disclosure.

The disclosure is based inter alia on the idea that the foot-operated control unit is typically of a completely cableless design and does not require connection by way of a cable during the as-intended operating mode or when in the not-in-use position. At the same time, it can in particular be ensured for the not-in-use position that the foot-operated control unit is easily arranged in a predetermined location and is consequently easily available for the as-intended use in the medical treatment system. In this case, the inclined bearing surface of the console makes it possible that, in the state in which it is arranged on the console, the foot-operated control unit already bears against the bearing surface of the console as a result of its weight, and consequently a reliable connection between the console and the foot-operated control unit can be achieved, and so when the system is not in the as-intended operating mode the console can be brought together with the foot-operated control unit. Its connection to the console allows the foot-operated control unit to be taken along with it. A handling unit which facilitates use can therefore be provided. Separate storage locations no longer have to be provided for the foot-operated control units. The provision of a console for a medical treatment also allows the foot-operated control unit to be provided at the same time. Particularly advantageously, the disclosure makes it possible to individually put together a cableless foot-operated control unit with a console as a combined unit. As a result, particular function-specific features of a respective medical treatment system can also be reliably realized in an easy way. Altogether, the disclosure thus makes it possible to improve the handling of a cableless foot-operated control unit.

The side wall of the housing which provides the bearing surface may be formed as a closed side wall. In addition, it may however also at least partially have one or more through-openings. The through-openings may also be provided in the region of the bearing surface. The housing, in particular the side wall, may be formed from a suitable stable material, for example metal, plastic, a composite material, combinations thereof and/or the like. In this case, an electrically conductive housing has the advantage that on the one hand an emission of disturbances with respect to electromagnetic compatibility on the console side can be minimized or even avoided and on the other hand influencing of the console, in particular the control unit, by electromagnetic signals from outside the console can be damped or suppressed. The reliability of the function of the medical treatment system can be improved as a result.

The side wall has in the region of the bearing surface the console-side connecting unit for releasably connecting the foot-operated control unit to the console. For this purpose, a retaining strip may be arranged for example in a lower region of the bearing surface. The retaining strip may also be combined with further connecting elements such as pins, clearances and the like. As a result of the inclined bearing surface, the foot-operated control unit need not be received in something like a receiving recess. As a result, the foot-operated control unit is particularly easily available and connectable to the console. The inclination of the bearing surface with respect to the horizontal plane is typically such that the bearing surface is facing away from the horizontal plane in the region of the foot of the console. It is already sufficient here for there to be a slight inclination with respect to the vertical, which may for example lie in a range from approximately 3° to approximately 15°, typically in a range from approximately 5° to approximately 10°.

The console has a charging unit for charging an electrical energy store of the foot-operated control unit, wherein the bearing surface has a charging connection with at least two electrical contacts for contacting corresponding mating contacts of the foot-operated control unit. It can in this way be achieved that the energy store of the foot-operated control unit can be charged in the not-in-use position in which the foot-operated control unit is arranged on the console. As a result, the foot-operated control unit can therefore be additionally made operationally ready for use as intended or be kept operationally ready. This can be achieved without additional electrical connecting means having to be actuated in order to make charging of the electrical energy store possible by way of the console. Just the arrangement of the foot-operated control unit on the bearing surface of the console can at the same time also realize an electrical coupling between the charging unit of the console and the electrical energy store of the foot-operated control unit. The charging unit may in principle be formed just by an electrical connection to an electrical energy source such as the public energy supply grid or the like. Typically, however, the charging unit also includes an energy converter, in order to be able to supply electrical energy to the energy store whenever required. This dispenses with the need for energy conversion in the foot-operated control unit. The energy converter may for example realize voltage matching between the voltage source and the energy store. For this purpose, at least two electrical contacts are provided in the region of the bearing surface, and so when the foot-operated control unit is arranged on the console at the same time an electrical connection of the foot-operated control unit to the console, in particular to its charging unit, can also be realized. For this purpose, the foot-operated control unit has corresponding mating contacts. The electrical contacts may for example be formed as pin contacts, which project outwardly from the plane of the bearing surface. The electrical contacts may for example be resiliently mounted. Of course, further contacts may also be provided, for example in order to be able to detect the foot-operated control unit, in particular its correct position on the bearing surface.

The bearing surface has a peripheral collar, which projects from the bearing surface and surrounds the electrical contacts. The collar may be formed from the same material as the side wall. The collar may be formed in one piece with the side wall. Alternatively, however, the collar may also be formed as a separate component which is fastened to the side wall at the predetermined position. In the circumferential direction, the collar may have a predeterminable inner and/or outer contour. The collar typically has a height which corresponds to at least the maximum height of the electrical contacts. As a result, the electrical contacts can be protected from external mechanical effects and particularly from fluid, such as for example aspiration fluid or irrigation fluid, which may run down on the side wall. The collar consequently provides good protection for the electrical contacts from corrosion, whereby it can be ensured that the electrical contacts function reliably for a long time.

The connecting unit has at least two retaining pins for arranging in corresponding receiving openings of the foot-operated control unit, which are arranged at least horizontally spaced-apart from one another. The retaining pins allow improved mounting of the foot-operated control unit on the console to be achieved. In particular, it can be achieved that it can be arranged on the console and removed from the console particularly easily. The retaining pins are typically dimensioned with respect to their length in such a way that they do not protrude through the foot-operated control unit in the state in which it is arranged on the console. The retaining pins may have a predeterminable contour with respect to a cross section which is formed as adapted to an inner contour of the receiving openings of the foot-operated control unit. In this way the foot-operated control unit and the console can be made to match one another, and so not just any foot-operated control unit can be combined with any console. This can of course also be achieved by the arrangement of the retaining pins, the number of retaining pins or the like. Typically, the retaining pins are of substantially the same design. In addition, it is preferred if the retaining pins project substantially perpendicularly out of the bearing surface. The retaining pins may be formed from the same material as the side wall. They may in particular be formed in one piece with the side wall. It may however also be provided that the retaining pins are separate parts which can be connected to the side wall, for example with a screwed connection, a riveted connection and/or the like.

It is also provided that the electrical contacts are formed as resilient electrical pin contacts. As a result, a reliable electrical contact can be ensured even in the case of variable positions of the mating contacts of the foot-operated control unit.

With respect to the foot-operated control unit, it is provided that the connecting region has at least two receiving openings for receiving corresponding retaining pins of the console, which are arranged at least horizontally spaced-apart from one another. This allows the foot-operated control unit to be arranged on the console and removed from the console in an easily performed way. It can also be achieved by the retaining pins engaging in the receiving openings that the foot-operated control unit can be protected from twisting under the effect of external forces in the state in which it is arranged on the console.

The charging unit has a charging connection with at least two electrical mating contacts, arranged at the connecting region, for contacting corresponding electrical contacts of the console. As a result, an electrical connection which allows the electrical energy store to be charged can be established in the state in which the foot-operated control unit is arranged on the console. The charging unit may in principle be formed just by an electrical connection. In addition, the charging unit may however also have an electrical energy converter, with which matching of an electrical voltage to the electrical energy store can be achieved. The charging unit may be designed for a unidirectional energy supply. The charging unit is typically electrically coupled to the electrical energy store.

It is also provided that the connecting region has a plateau for arranging in a clearance provided through the collar, wherein the electrical mating contacts are arranged in the region of a plateau plane of the plateau. As a result, it can be achieved that the electrical connection is protected from external effects in the state in which the foot-operated control unit is arranged on the console. This is advantageous in particular whenever, during a charging operation of the electrical energy store, an operating voltage between the electrical contacts is greater than an extra-low voltage as defined by standards. The extra-low voltage may for example correspond to the Directive 2001/95/EC of the European Parliament and of the Council of Dec. 3, 2001 on general product safety. This is typically an AC voltage with a root-mean square value of less than approximately 50 V or a DC voltage of less than approximately 75 V.

The arrangement of the electrical mating contacts on the plateau surface makes them particularly easily accessible for any cleaning processes. It may also be provided for the electrical mating contacts that they are resiliently mounted. The electrical mating contacts are typically formed by flat, electrically conductive elements, which can establish a good electrical contact with the electrical contacts of the console. They are particularly advantageously designed for contacting contact pins.

The advantages and effects indicated for the console according to the disclosure and the foot-operated control unit according to the disclosure are of course also equally applicable to the medical treatment system fitted out with the console according to the disclosure and the foot-operated control unit according to the disclosure, and vice versa.

Further features of the disclosure are evident from the figures and the description of the figures. The features and combinations of features mentioned in the description above and the features and combinations of features mentioned in the description of the figures below and/or shown only in the figures can be used not only in the respectively specified combination but also in other combinations, without departing from the scope of the disclosure. Consequently, exemplary embodiments of the disclosure which are not explicitly shown and explained in the figures but emerge from and can be created by separate combinations of features from the explained exemplary embodiments should also be considered to be included and disclosed.

BRIEF DESCRIPTION OF THE DRAWINGS

The disclosure will now be described with reference to the drawings wherein.

DESCRIPTION OF EXEMPLARY EMBODIMENTS

Figure 1:
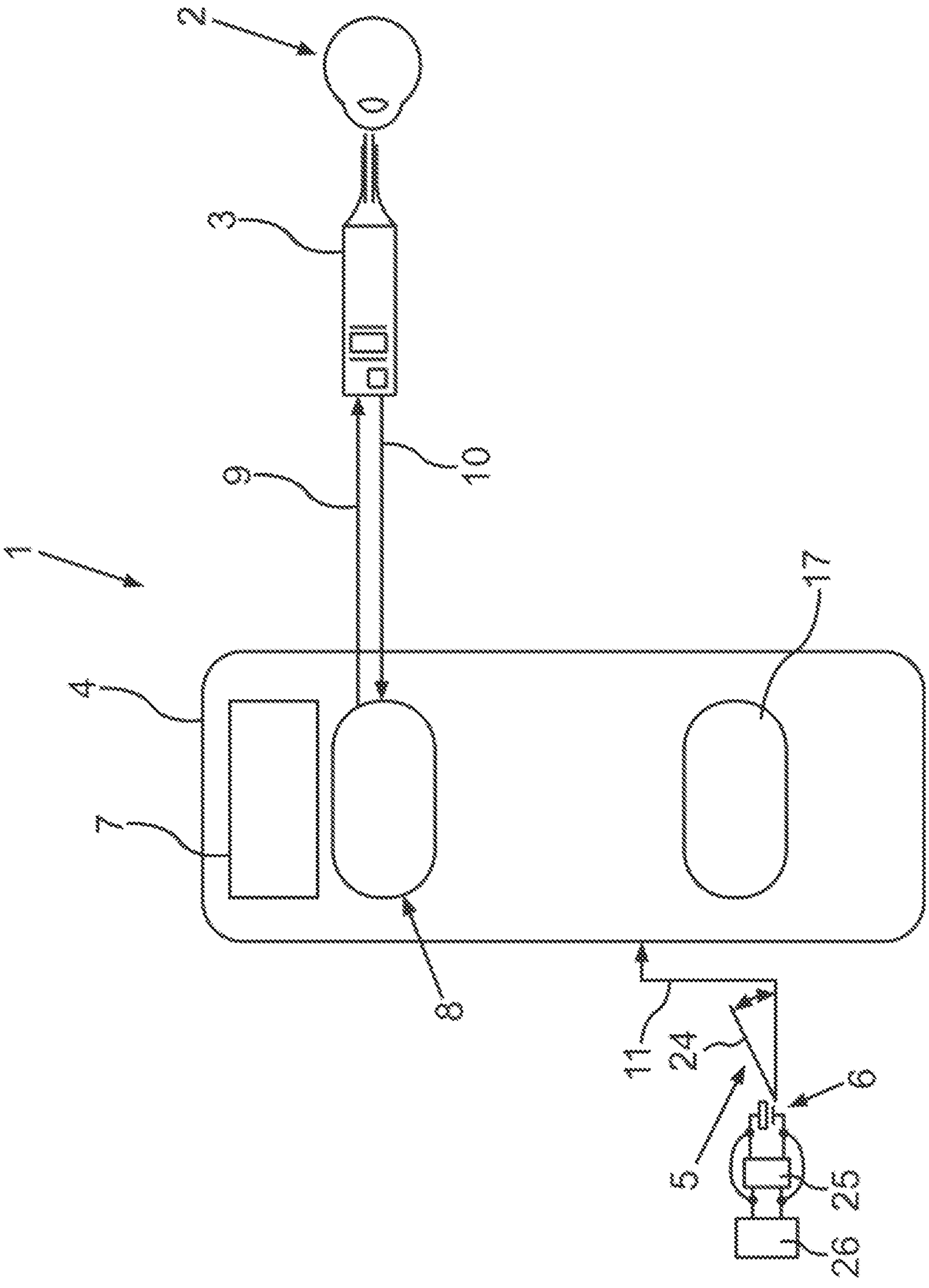
FIG. 1 shows a schematic representation of an exemplary embodiment of an ophthalmosurgical system with a console, a foot-operated control unit and also a handpiece connected to the console.

FIG. 1 shows in a schematic block diagram an ophthalmosurgical system 1 as a medical treatment system which serves for the treatment of an eye 2. The ophthalmosurgical system 1 has a medical treatment instrument, which in the present case is formed by a handpiece 3. The ophthalmosurgical system 1 also has a console 4 for connecting and operating the handpiece 3 during an as-intended operating mode. Furthermore, the ophthalmosurgical system 1 has a foot-operated control unit 5, which in the present case is formed as a foot pedal. The foot-operated control unit 5 can be coupled wirelessly to the console 4 by way of a radio connection 11 and has an electrical energy store 6 for supplying the foot-operated control unit 5 with electrical energy, at least during the as-intended operating mode of the handpiece 3.

The console 4 also has a control unit 7 and also fluidic and electrical supply units 8, which serve inter alia for feeding an irrigation fluid to the handpiece 3 by way of an irrigation line 9 and discharging an aspiration fluid from the handpiece 3 by way of an aspiration line 10.

The foot-operated control unit 5 in the present case is of a cableless design, for which reason it is supplied with electrical energy from the electrical energy store 6, at least during the as-intended operating mode. In addition, during the as-intended operating mode, the foot-operated control unit 5 is in communication connection with the control unit 7 by way of the wireless radio connection 11, and so an operating state of the handpiece 3 can be at least partially set.

Figure 2:
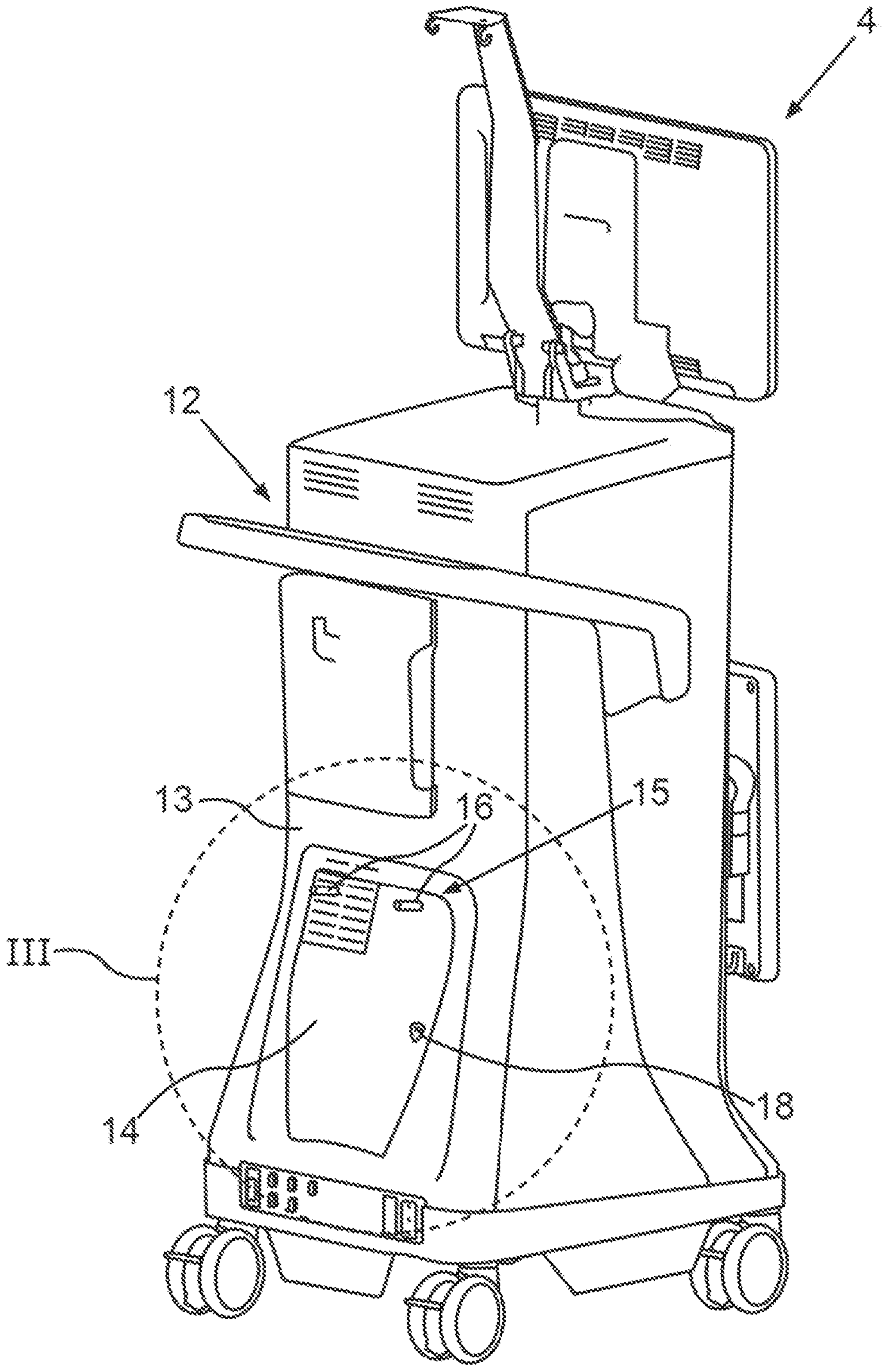
FIG. 2 shows a schematic perspective representation of the console according to FIG. 1.

FIG. 2 shows the console 4 according to FIG. 1 in a schematic-perspective view which includes the rear side. The console 4 has a console housing 12, in which the elements or units of the console 4 are arranged. The console housing 12 has a side wall 13, which in the present case forms a rear side of the console 4. The side wall 13 has a bearing surface 14, which serves for arranging the foot-operated control unit 5 in a not-in-use position. The bearing surface 14 is inclined with respect to a horizontal plane in the region where the foot-operated control unit 5 is arranged, in order when arranging the foot-operated control unit 5 on the bearing surface 14 to bring about bearing of the foot-operated control unit 5 against the bearing surface 14 by the weight of the foot-operated control unit 5. In the present case, the bearing surface 14 is of a planar or flat design, in particular uncurved.

Figure 3:
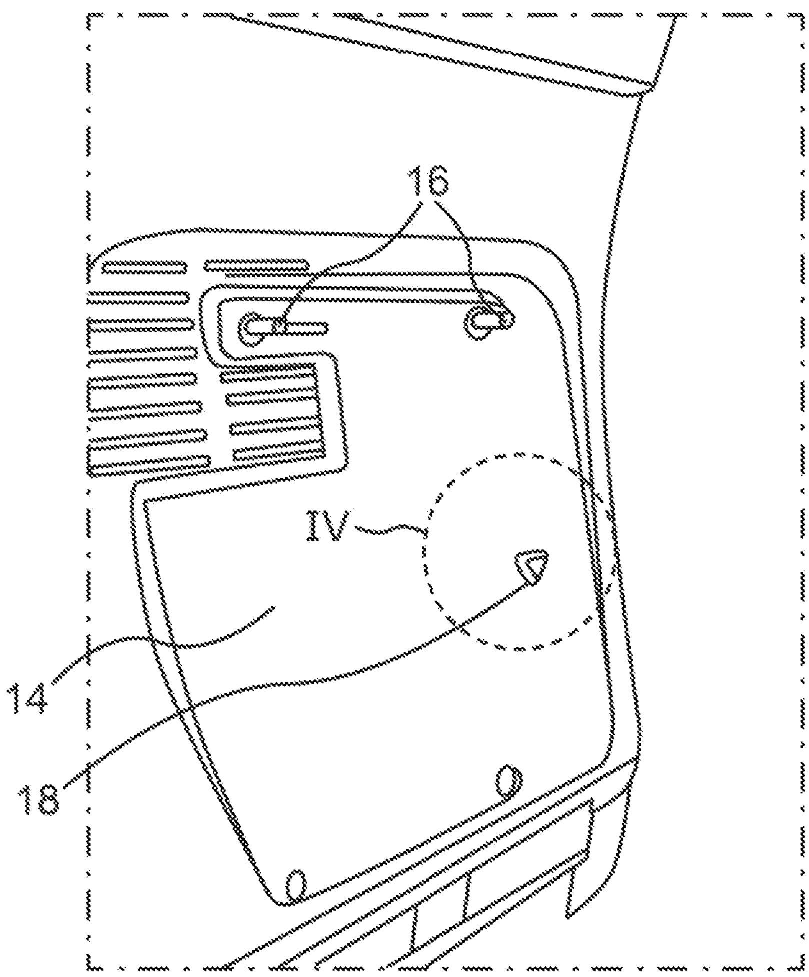
FIG. 3 shows a schematic-perspective representation of a side wall in a lower region of the console according to FIG. 1.
Figure 4:
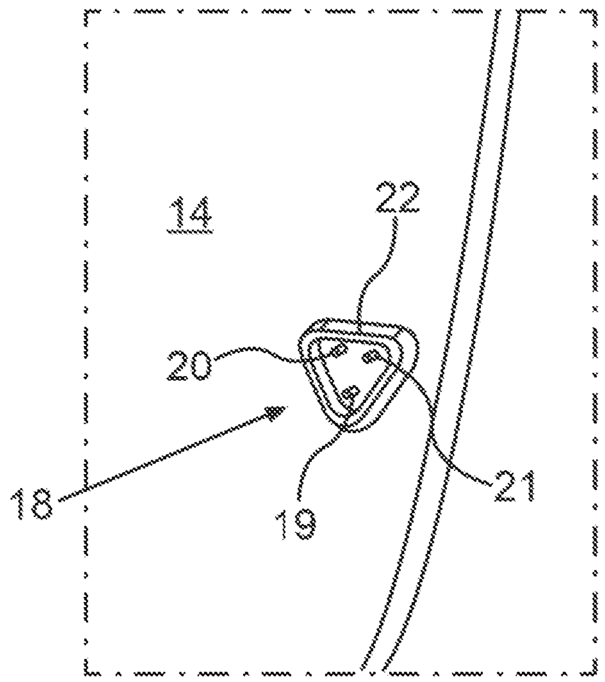
FIG. 4 shows an enlarged representation of a region IV from FIG. 3.

To be able to keep the foot-operated control unit 5 in the state in which it is arranged on the console 4, the side wall 13 has in the region of the bearing surface 14 a console-side connecting unit 15 for releasably connecting the foot-operated control unit 5 to the console 4. For this purpose, the console-side connecting unit 15 has two retaining pins 16 for arranging in corresponding receiving openings of the foot-operated control unit 5, which are arranged horizontally spaced-apart from one another. In the present case, it is provided that the retaining pins 16 are arranged at substantially approximately the same height with respect to a horizontal base. In alternative configurations, this may however also differ. FIG. 3 shows a corresponding enlarged representation of a detail III in FIG. 2. FIG. 4 shows in a schematic plan view an enlarged representation of a region IV in FIG. 3. It can be seen that the bearing surface 14 has a peripheral collar 22, which projects from the bearing surface 14 and surrounds electrical contacts 19, 20, 21.

The console 4 also has a charging unit 17 for charging the electrical energy store 6 of the foot-operated control unit 5. The bearing surface 14 has a charging connection 18 of the charging unit 17 with three electrical contacts 19, 20, 21 for contacting corresponding electrical mating contacts 31, 32, 33 of the foot-operated control unit 5 (FIG. 5).

In the present configuration, it is provided that the electrical contacts 19, 20, 21 are fixedly connected to the bearing surface 14. In alternative configurations, it may be provided that the electrical contacts 19, 20, 21, which are formed as pin contacts, may also be formed as resilient electrical contacts.

The electrical contacts 19, 20, 21 are arranged as electrically insulated with respect to the side wall 13. The electrical contacts 19, 20, 21 are connected to the charging unit 17.

Figure 5:
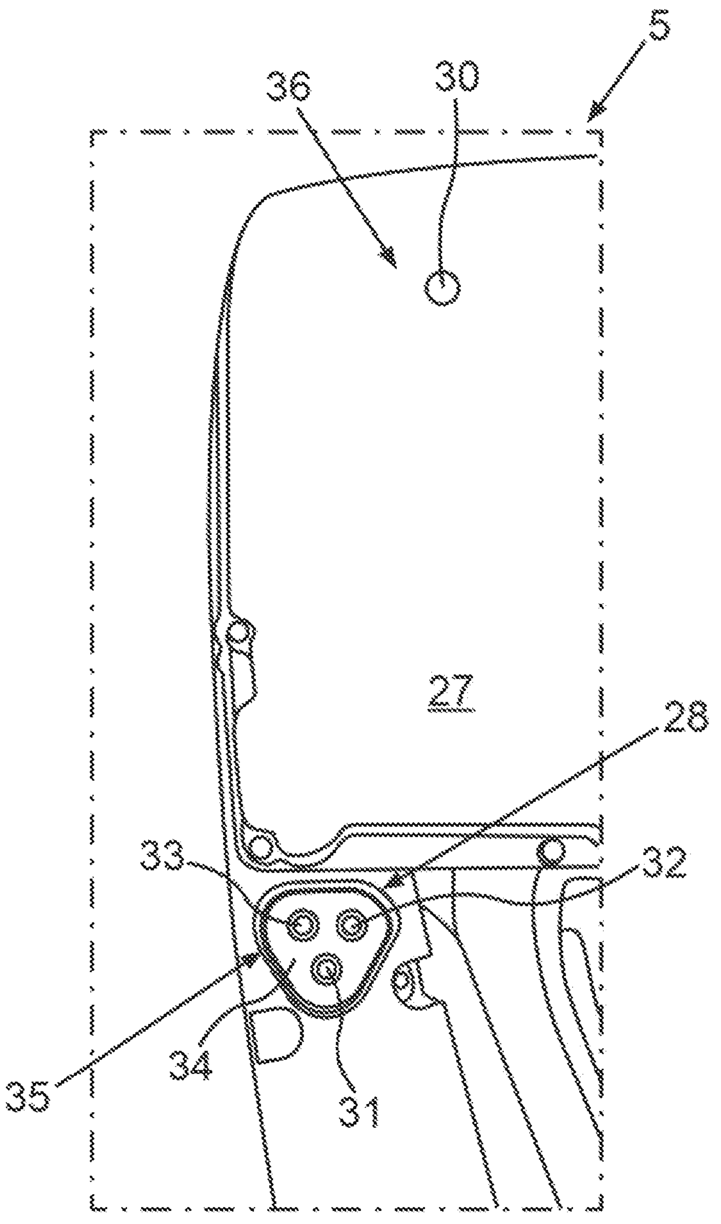
FIG. 5 shows a schematic plan view of a rear side of the foot-operated control unit according to FIG. 1 in the region of electrical mating contacts.
Figure 6:
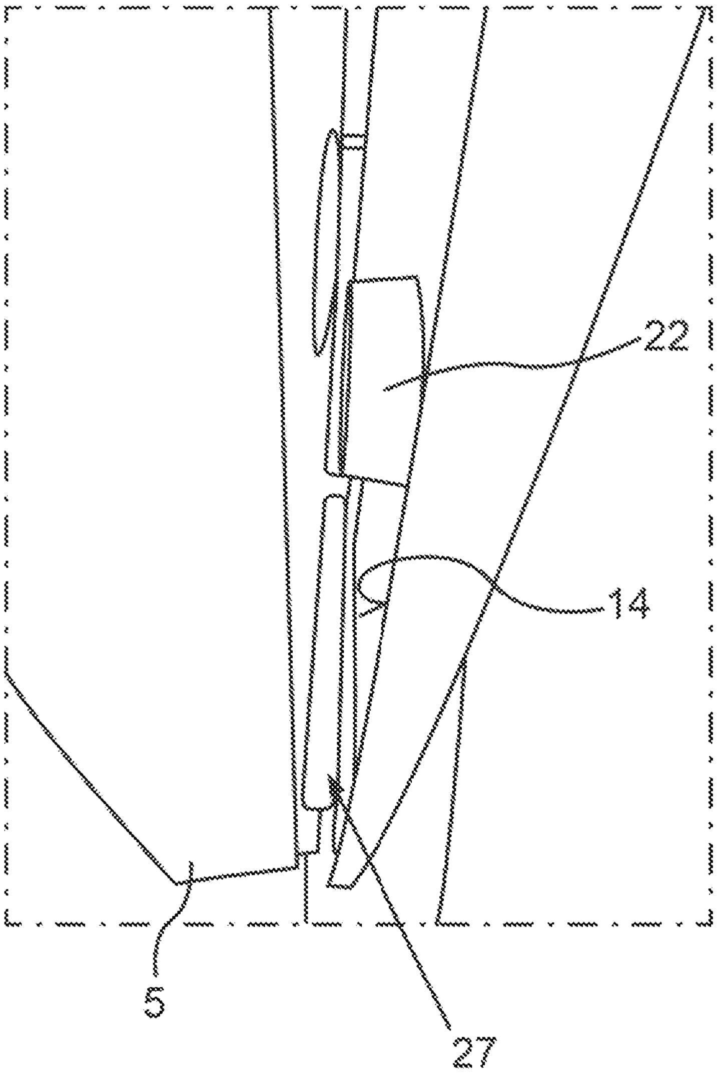
FIG. 6 shows a schematic side view of a detail of a foot-operated control unit positioned at a distance from the console in the region of the bearing surface.
Figure 7:
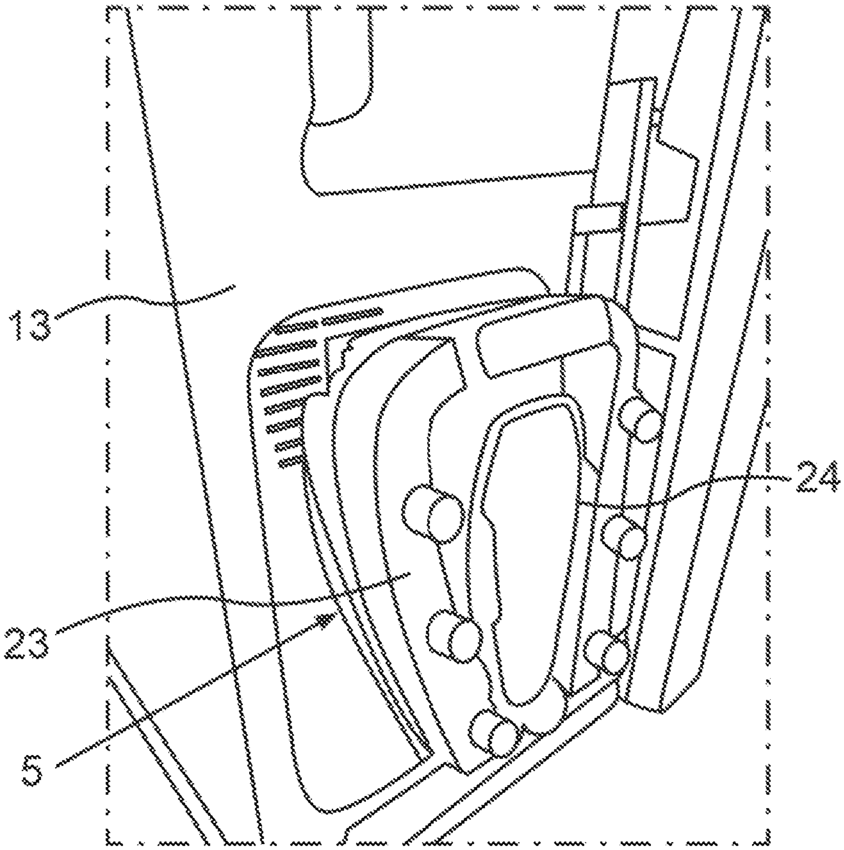
FIG. 7 shows a schematic-perspective representation as in FIG. 3, wherein the foot-operated control unit is arranged on the console.

FIG. 5 shows in a schematic plan view a detail of a rear side of the foot-operated control unit 5. The foot-operated control unit 5 has a housing 23 (FIG. 7), an electrical energy store 6 arranged in the housing 23 (FIG. 1), an actuating element 24 which can be actuated with a foot (FIG. 1), a communication unit 26 for wireless communication by radio with the console 4 of the ophthalmosurgical system 1 and also a charging unit 25 for charging the electrical energy store 6 (FIG. 1). The housing 23 has a connecting region 27 for releasably arranging the foot-operated control unit 5 in a not-in-use position on the bearing surface 14 of the console 4 (FIG. 6)

The connecting region 27 has a connecting unit 36 on the foot-operated control unit side for releasably connecting the foot-operated control unit 5 to the console 4. The connecting region 27 has two receiving openings 30 for receiving corresponding retaining pins 16 of the console 4, which are arranged at least horizontally spaced-apart from one another. As a result, the foot-operated control unit 5 can be easily arranged on the console 4, wherein the retaining pins 16 are inserted into the receiving openings 30 formed as blind holes. The simultaneous inclined position of the bearing surface 14 consequently allows a reliable, releasable connection to the console 4 to be achieved by the weight of the foot-operated control unit 5.

The charging unit 25 has a charging connection 28, which has the three electrical mating contacts 31, 32, 33, arranged at the connecting region 27, for contacting corresponding electrical contacts 19, 20, 21 of the console 4. The electrical mating contacts 31, 32, 33 are formed in the present case as flat, substantially circular contact plates, which are connected to the charging unit 25 by way of electrical lines that are not shown.

The connecting region 27 has the plateau 35 for arranging in a clearance provided through the collar 22. The electrical mating contacts 31, 32, 33 are arranged in the region of a plateau plane 34 of the plateau 35. The arrangement corresponds to the arrangement of the electrical contacts 19, 20, 21, and so an electrical connection can be achieved by respective contacting when the foot-operated control unit 5 is arranged on the console 4. They are resiliently mounted in the present case, but in alternative configurations may also be fixedly connected to the plateau 35.

The disclosure can achieve the effect in particular of fitting out a modern workplace for performing a cataract operation. The units or systems of the ophthalmosurgical system are interconnected in order to make good performance and easy, intuitive operator control possible. The disclosure allows cable connections or hose connections for fluids to be at least partially avoided. In particular, electrical cable connections and also communication lines can be avoided almost completely. For this purpose, a wireless communication connection to the console 4 is provided for the foot-operated control device 5, also known as a foot-switch pedal (FSP). This however requires that the foot-operated control device or the foot-operated control unit 5 also has an at least partially independent energy supply, for which reason the electrical energy store 6 is provided, usually formed as a storage battery.

When the ophthalmosurgical system 1 is not in the as-intended operating mode, the disclosure allows the foot-operated control device 5 to be stored as a combined unit with the console 4. The aforementioned connecting technique allows a manageable unit comprising the console 4 and the foot-operated control unit 5 to be created when it is not in the as-intended operating mode, and so the corresponding devices for an ophthalmosurgical operation can be provided in an easy way.

In addition, the disclosure makes it possible to supply the foot-operated control device 5, in particular its energy store 6, with electrical energy when it is arranged in the not-in-use position on the console 4. The electrical contact connection provided here allows a reliable line-bound, but at the same time cableless electrical connection to be achieved, and so a large amount of energy can also be easily transmitted in a short time. This largely allows the avoidance of disturbances such as can occur for example during energy transmission using alternating magnetic fields. This is particularly important for the medical sector.

The electrical mating contacts 31, 32, 33 are in the present case bonded in the housing 23 by being adhesively attached on an underside. They may alternatively also be molded in, if for example the housing 23 is formed from a plastic.

In the present case, it is provided that the electrical voltage between the mating electrodes 31, 32, 33 and the electrical contacts 19, 20, 21 is approximately 15 V. This is a DC voltage. A charging current may be for example approximately 1 A. In addition, a protective function may be achieved in each case by way of the third electrical contact 19 or electrical mating contact 31, and so the supply voltage of 15 V is only made available when an electrical contact has been established by way of these two electrical contacts 19, 31. If an electrical contact cannot be established by way of these contacts, it may be provided that the electrical voltage is limited to approximately 3.3 V or is even switched off completely. This can be sensed by the charging unit 17, for which purpose the charging unit 25 applies a corresponding signal to the electrical mating contact 31. The charging function can then take place for example by way of the electrical contacts 20, 21 or 32, 33. As a result, it can for example also be achieved that an electrical voltage is only applied to the electrical contacts 20, 21 whenever the charging unit 17 detects a corresponding connection by the foot-operated control unit 5 being arranged on the console 4.

In addition, it may be provided that the electrical voltage is provided as a safety extra-low voltage. Increased safety can be achieved as a result.

The collar 22 interacts with the plateau 35 when the foot-operated control unit 5 is arranged on the console 4. This can inter alia achieve a centering effect if an inner contour of the clearance provided through the collar 22 is chosen as adapted to an outer contour of the plateau 35. As a result, centering of the electrical contacts or electrical mating contacts can also be achieved. In addition, the collar 22 can protect the electrical contacts 19 to 21 from external mechanical effects.

In addition, it is provided that the charging unit 17 is designed to evaluate an electrical potential at at least one of the electrical contacts 19, 20, 21 in order to detect that the foot-operated control unit 5 is arranged on the console 4. This can be used to obtain the effect that the charging unit 17 only applies an electrical voltage to the electrical contacts 19, 20, 21 whenever it has been detected that the foot-operated control unit 5 is correspondingly arranged on the console 4. As a result, the electrical safety can be improved. It is of course also possible for the purposes of detection for potential differences between pairs of the electrical contacts 19, 20, 21 to be evaluated.

It is understood that the foregoing description is that of the exemplary embodiments of the disclosure and that various changes and modifications may be made thereto without departing from the spirit and scope of the disclosure as defined in the appended claims.

LIST OF REFERENCE NUMERALS

1 Ophthalmosurgical system
2 Eye
3 Handpiece

4 Console
5 Foot-operated control unit
6 Energy store
7 Control unit
8 Supply units
9 Irrigation line
10 Aspiration line
11 Radio connection
12 Console housing
13 Side wall
14 Bearing surface
15 Connecting unit
16 Retaining pin
17 Charging unit
18 Charging connection
19 Electrical contact
20 Electrical contact
21 Electrical contact
22 Collar
23 Housing
24 Actuating element
25 Charging unit
26 Communication unit
27 Connecting region
28 Charging connection
30 Receiving opening
31 Electrical mating contact
32 Electrical mating contact
33 Electrical mating contact
34 Plateau plane
35 Plateau
36 Connecting unit

What is claimed is:

1. A console for a medical treatment system or an ophthalmosurgical system for the treatment of an eye, the console comprising:

a console housing; and a control unit configured to control a medical treatment instrument, wherein a foot-operated control unit can be wirelessly coupled to the control unit, and the console housing has at least one side wall, wherein the side wall has a bearing surface for arranging the foot-operated control unit on the bearing surface in a not-in-use position, wherein the bearing surface is inclined with respect to a horizontal plane, at least in the region where the foot-operated control unit is to be arranged, in order to effect abutting of the foot-operated control unit against the bearing surface by a weight of the foot-operated control unit when the foot-operated control unit is arranged at the bearing surface, wherein the bearing surface has an inclination with respect to a vertical plane in the range between 3° and 15°, wherein the side wall has a console-side connecting unit for releasably connecting the foot-operated control unit to the console in the region of the bearing surface, wherein the console has a charging unit for charging an electrical energy store of the foot-operated control unit, wherein the bearing surface has a charging connection with at least two electrical contacts for contacting corresponding mating contacts of the foot-operated control unit, wherein the bearing surface has a circumferential collar, which projects from the bearing surface and entirely surrounds the electrical contacts, wherein the electrical contacts are formed as resilient electrical pin contacts which are connected to the charging unit via electrical lines, and wherein the console-side connecting unit has at least two retaining pins for arranging in corresponding receiving openings of the foot-operated control unit, which are arranged at least horizontally spaced-apart from one another on the bearing surface such that when the foot-operated control unit is releasably arranged on the bearing surface, the at least two retaining pins predefine a position of the foot-operated control unit in which the resilient electrical pin contacts are held in contact with electrical mating contacts of the foot-operated control unit due to a weight of the foot-operated control unit acting on the at least two retaining pins, and such that the foot-operated control unit is protected from twisting caused by external forces.

2. The console as claimed in claim 1, wherein the charging unit is configured to evaluate an electrical potential at at least one of the electrical contacts to detect that the foot-operated control unit is arranged on the console.

3. A medical treatment system for the treatment of an eye, the medical treatment system comprising:

a medical treatment instrument;

a console configured for connecting and operating the medical treatment instrument during an as-intended operating mode; and a foot-operated control unit for at least partially controlling the as-intended operating mode of the medical treatment instrument, wherein the foot-operated control unit can be wirelessly coupled to the console and has an electrical energy store for supplying the foot-operated control unit with electrical energy, at least during the as-intended operating mode of the medical treatment system, and wherein at least the console is configured as claimed in claim 1.

4. The console as claimed in claim 1, wherein the resilient electrical pin contacts are formed as flat, substantially circular contact plates.

5. The console as claimed in claim 1, wherein the retaining pins protrude perpendicularly from the bearing surface.

6. The console as claimed in claim 1, wherein the retaining pins protrude from the bearing surface, wherein the corresponding receiving openings are blind holes, and wherein when the foot-operated control unit is releasably arranged on the bearing surface, the at least two retaining pins predefine a position of the foot-operated control unit in which the resilient electrical pin contacts are held in contact with electrical mating contacts of the foot-operated control unit by gravitation force acting on the at least two retaining pins, and such that the foot-operated control unit is protected from twisting caused by external forces other than the gravitation force.

7. A foot-operated control unit for a medical treatment system or an ophthalmosurgical system for the treatment of an eye, the foot-operated control unit comprising:

a housing;

an electrical energy store arranged in the housing;

an actuating element which can be actuated with a foot;

a communication unit configured for wireless communication with a console of the medical treatment system; and a charging unit for charging the electrical energy store, wherein the housing has a connecting region for releasably arranging the foot-operated control unit in a not-in-use position on a bearing surface of the console, wherein the connecting region has a connecting unit on the foot-operated control unit side for releasably connecting the foot-operated control unit to the console, wherein the charging unit has a charging connection with at least two electrical mating contacts, arranged at the connecting region, for contacting corresponding electrical contacts of the console, and wherein the connecting region has at least two receiving openings for receiving corresponding retaining pins of the console, which are arranged at least horizontally spaced-apart from one another such that when the foot-operated control unit is releasably arranged on the bearing surface of the console, the at least two receiving openings predefine a position of the foot-operated control unit in which the at least two electrical mating contacts are held in contact with corresponding electrical contacts of the console due to a weight of the foot-operated control unit acting on the corresponding retaining pins, and such that the foot-operated control unit is protected from twisting caused by external forces.

8. The foot-operated control unit as claimed in claim 7, wherein the connecting region has a plateau for arranging in a recess provided by a circumferential collar of the console, and wherein the electrical mating contacts are arranged in the region of a plateau plane of the plateau.

* * * * *